United States Patent
Koh

(10) Patent No.: US 10,035,734 B2
(45) Date of Patent: Jul. 31, 2018

(54) FOOD WASTE TREATMENT APPARATUS

(71) Applicant: James Chun Koh, Fort Lee, NJ (US)

(72) Inventor: James Chun Koh, Fort Lee, NJ (US)

( * ) Notice: Subject to any disclaimer, the term of this patent is extended or adjusted under 35 U.S.C. 154(b) by 236 days.

(21) Appl. No.: 15/067,152

(22) Filed: Mar. 10, 2016

(65) Prior Publication Data

US 2017/0260108 A1   Sep. 14, 2017

(51) Int. Cl.

| | |
|---|---|
| C12M 1/00 | (2006.01) |
| C12M 3/00 | (2006.01) |
| C05F 9/02 | (2006.01) |
| B01F 7/00 | (2006.01) |
| B01F 7/20 | (2006.01) |
| B01F 15/00 | (2006.01) |
| B09B 5/00 | (2006.01) |
| C12M 1/06 | (2006.01) |
| C12M 3/04 | (2006.01) |
| C05F 17/02 | (2006.01) |

(52) U.S. Cl.
CPC .............. *C05F 9/02* (2013.01); *B01F 7/0025* (2013.01); *B01F 7/00125* (2013.01); *B01F 7/00208* (2013.01); *B01F 7/00633* (2013.01); *B01F 7/20* (2013.01); *B01F 15/00538* (2013.01); *B09B 5/00* (2013.01); *C05F 17/0223* (2013.01); *C05F 17/0258* (2013.01); *C12M 27/02* (2013.01); *C12M 27/10* (2013.01); *B01F 2015/00623* (2013.01); *Y02P 20/145* (2015.11); *Y02W 30/43* (2015.05)

(58) Field of Classification Search
CPC ....... C12M 21/04; C12M 27/02; C12M 27/10
See application file for complete search history.

(56) References Cited

U.S. PATENT DOCUMENTS

| | | | | |
|---|---|---|---|---|
| 3,682,398 | A * | 8/1972 | Lamort ..................... | D21D 1/32 241/46.04 |
| 6,110,727 | A * | 8/2000 | Widmer .................... | B01F 3/06 210/603 |
| 6,168,711 | B1 * | 1/2001 | Teramachi ............. | B01D 53/84 210/123 |
| 7,735,761 | B2 | 6/2010 | Koh | |
| 7,762,713 | B2 | 7/2010 | Koh | |
| 2004/0031295 | A1 * | 2/2004 | Choi ........................ | D06F 25/00 68/24 |
| 2008/0227180 | A1 * | 9/2008 | Bovaird .................. | C02F 3/006 435/262.5 |
| 2012/0009668 | A1 * | 1/2012 | Hass ......................... | B09B 3/00 435/300.1 |
| 2013/0099034 | A1 * | 4/2013 | Koh ......................... | C05F 17/02 241/37.5 |

\* cited by examiner

*Primary Examiner* — Nathan A Bowers
(74) *Attorney, Agent, or Firm* — Leepi

(57) ABSTRACT

The present disclosure suggests a food waste treatment apparatus. A food waste treatment apparatus in accordance with an exemplary embodiment of the present disclosure includes: a housing including a food inlet opening at its top surface; an inner chamber where food introduced through the food inlet opening is collected; a stirring unit provided within the inner chamber and configured to stir food waste; an outer chamber positioned outside the inner chamber; and a rotation driving unit configured to rotate the stirring unit and the inner chamber, and the inner chamber and the stirring unit are rotated by the rotation driving unit in opposite directions.

15 Claims, 11 Drawing Sheets

FOOD WASTE TREATMENT APPARATUS

TECHNICAL FIELD

The present disclosure relates to a food waste treatment apparatus.

BACKGROUND

Generally, organic waste such as food waste contains a lot of proteins, carbohydrates, and calcium as well as animal/plant fibers. Therefore, if it is not buried without being degraded and destructed, extracts generated from the organic waste may flow into the ground and may pollute the groundwater or the like. Accordingly, a food waste treatment apparatus has been generally used for treating food waste.

Regarding such a food waste treatment apparatus, Korean Patent Application No. 10-2008-0008421 discloses "Food and drink waste for destruction equipment".

However, if food wastes are excessively put into a conventional food waste treatment apparatus, the food wastes cannot be stirred readily.

Further, in the conventional food waste treatment apparatus, solid sludge is formed at a drainage hole through which leachate is discharged. Therefore, as time goes on, the leachate cannot be discharged readily.

SUMMARY

In view of the foregoing, the present disclosure provides a food waste treatment apparatus with improved performance in treating food waste.

An aspect of the present disclosure provides a food waste treatment apparatus includes: a housing including a food inlet opening at its top surface; an inner chamber where food introduced through the food inlet opening is collected; a stirring unit provided within the inner chamber and configured to stir food waste; an outer chamber positioned outside the inner chamber; and a rotation driving unit configured to rotate the stirring unit and the inner chamber, and the inner chamber and the stirring unit are rotated by the rotation driving unit in opposite directions.

According to the above-described exemplary embodiment of the present disclosure, since a stirring unit and an inner chamber are rotated in opposite directions, the efficiency in stirring food waste can be improved, and, thus, the performance in treating food waste can be improved remarkably.

Further, the present food waste treatment apparatus includes multiple drainage holes at a circumferential portion and a bottom portion of the inner chamber, and, thus, the leachate drain performance and the destruction effect can be greatly increased.

Furthermore, the present food waste treatment apparatus has an effect of automatically cleaning the drainage holes through which leachate is discharged using a brush unit and a high-pressure cleaning unit.

Moreover, the present food waste treatment apparatus has an advantage of effectively discharging effluent and sludge collected in an outer chamber using a scrapper. The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
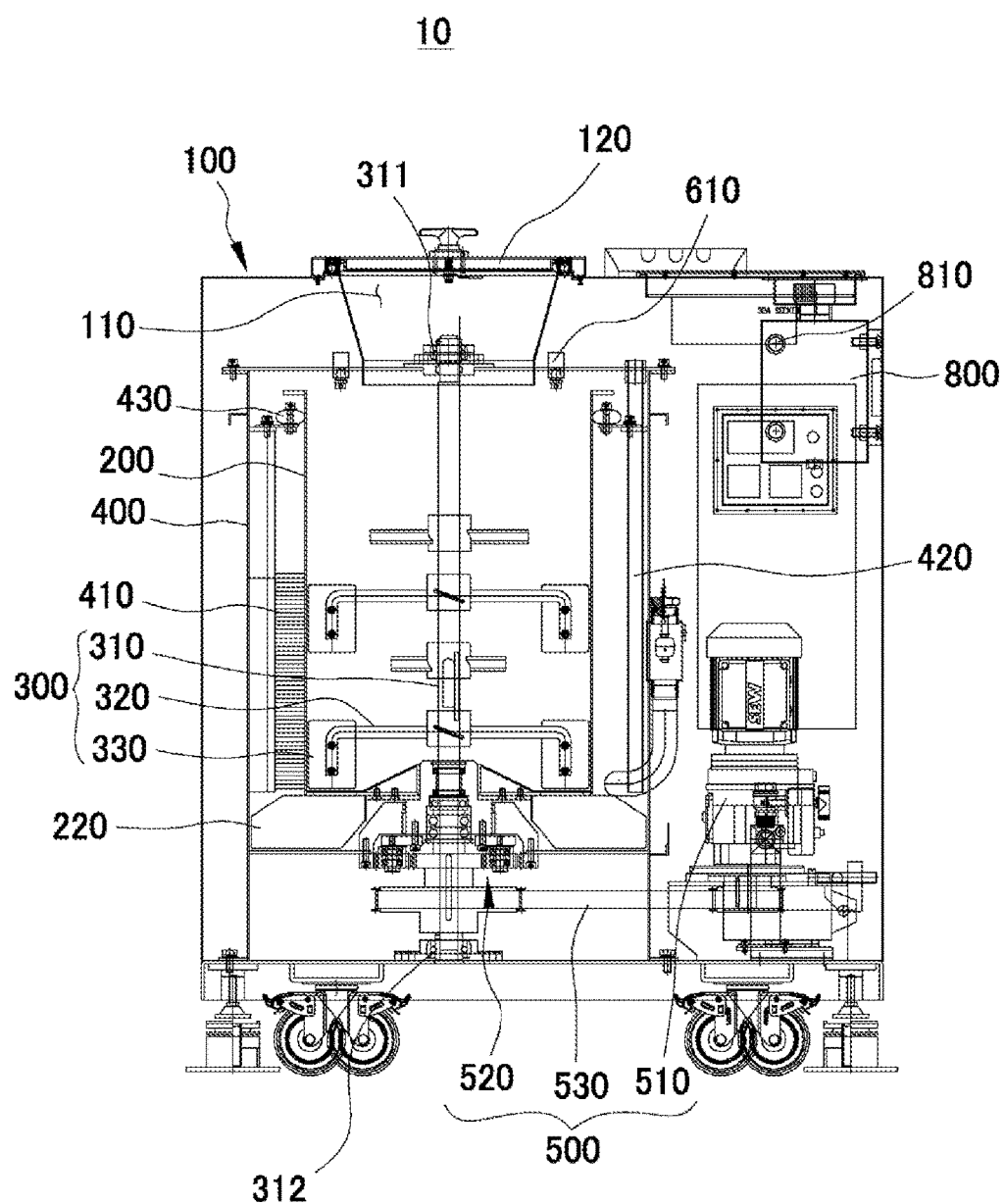
FIG. 1 is a front view of a food waste treatment apparatus in accordance with an exemplary embodiment of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the another element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

The present disclosure relates to a food waste treatment apparatus 10.

Figure 2:
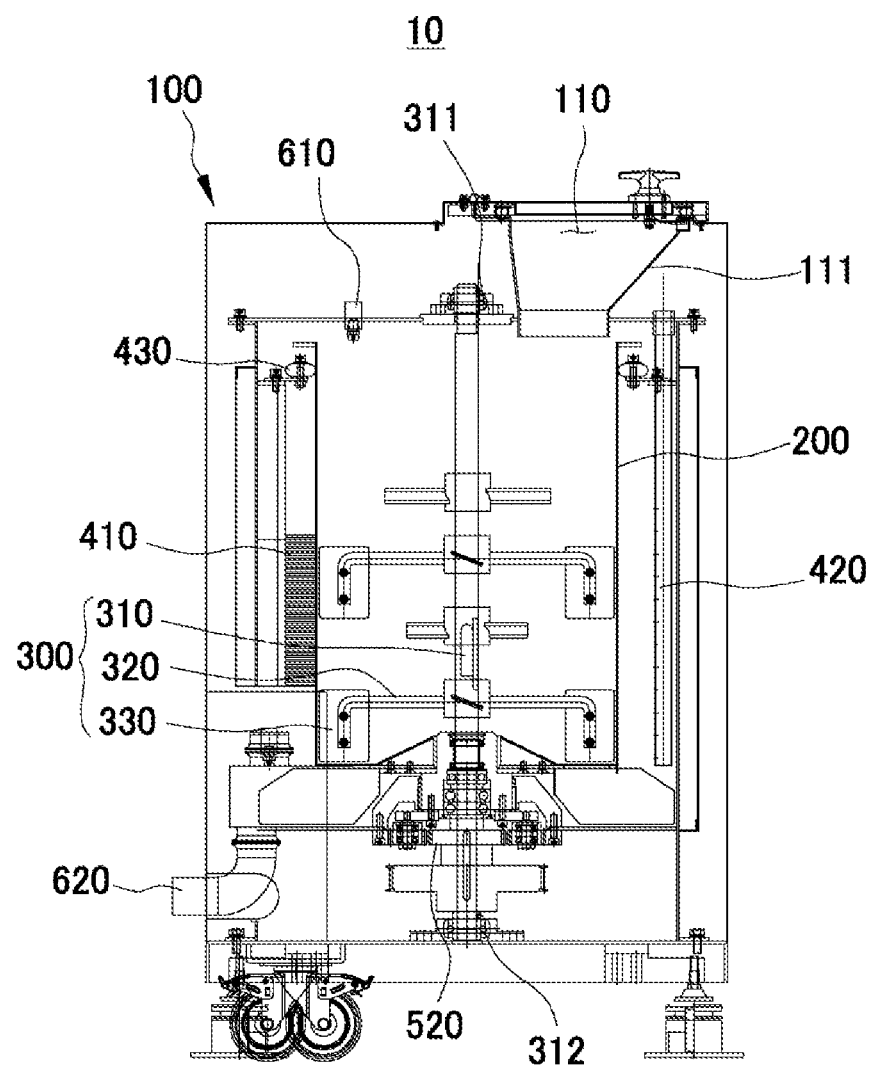
FIG. 2 is a side view of a food waste treatment apparatus in accordance with an exemplary embodiment of the present disclosure.
Figure 3:
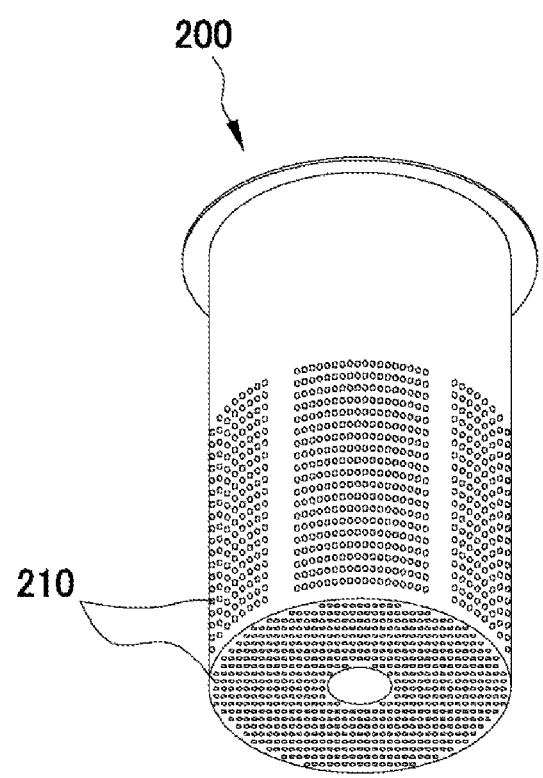
FIG. 3 is a perspective view of an inner chamber in accordance with an exemplary embodiment of the present disclosure.
Figure 4:
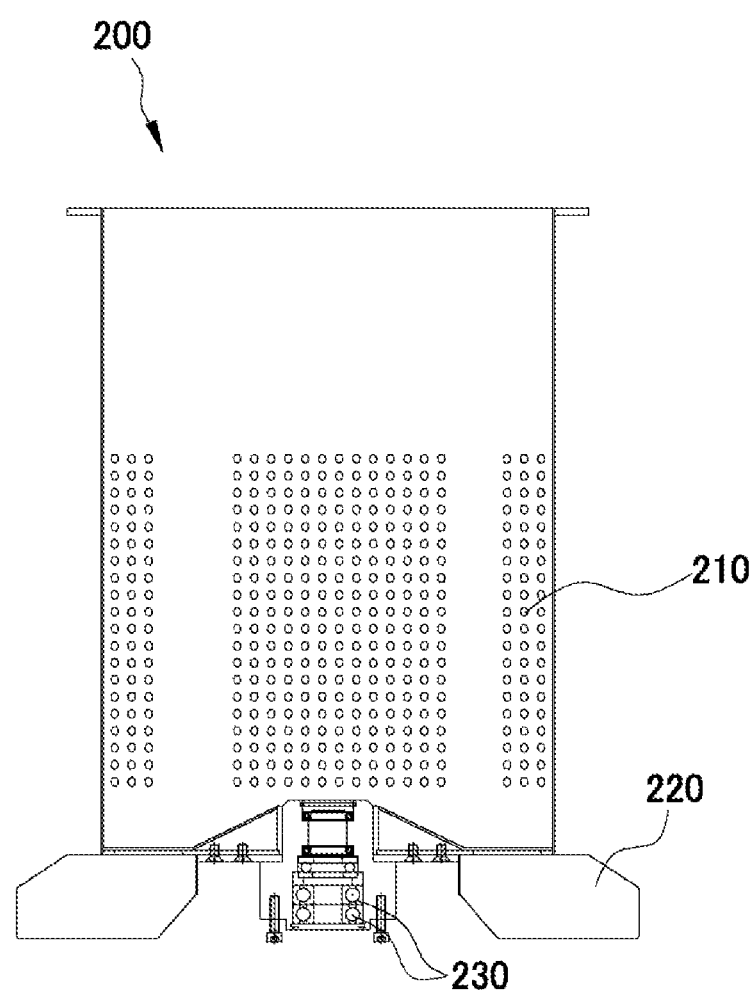
FIG. 4 is a cross-sectional view of an inner chamber in accordance with an exemplary embodiment of the present disclosure.
Figure 5:
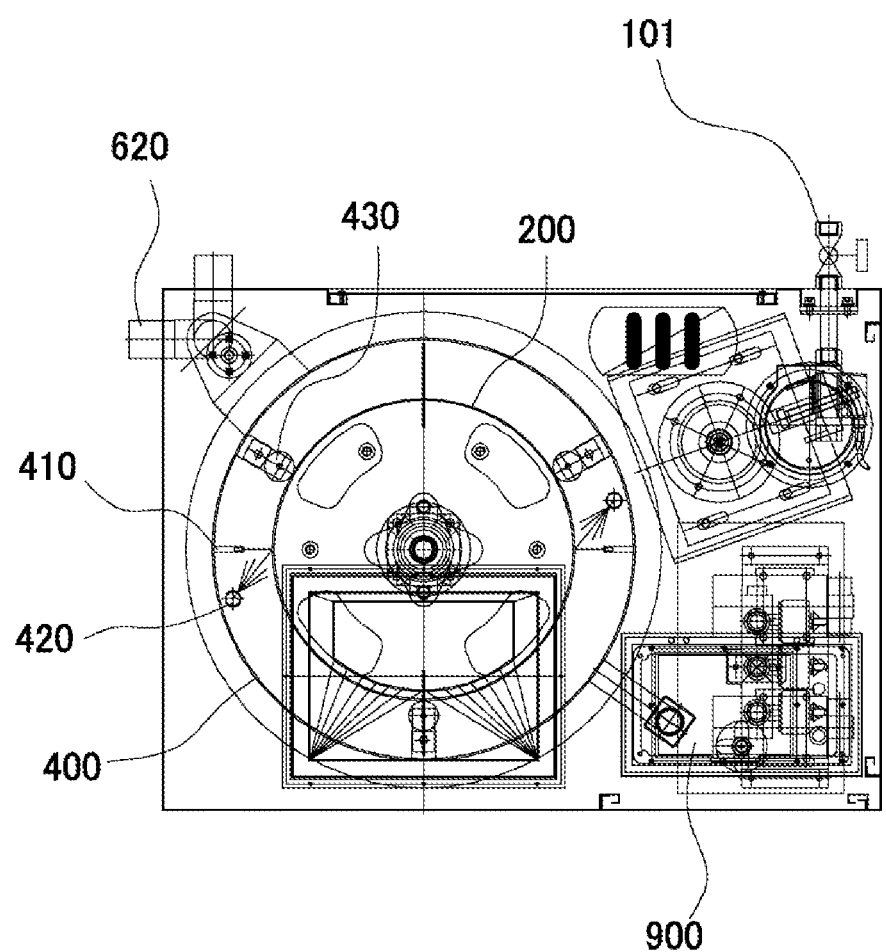
FIG. 5 is a plane view of a food waste treatment apparatus in accordance with an exemplary embodiment of the present disclosure.
Figure 6:
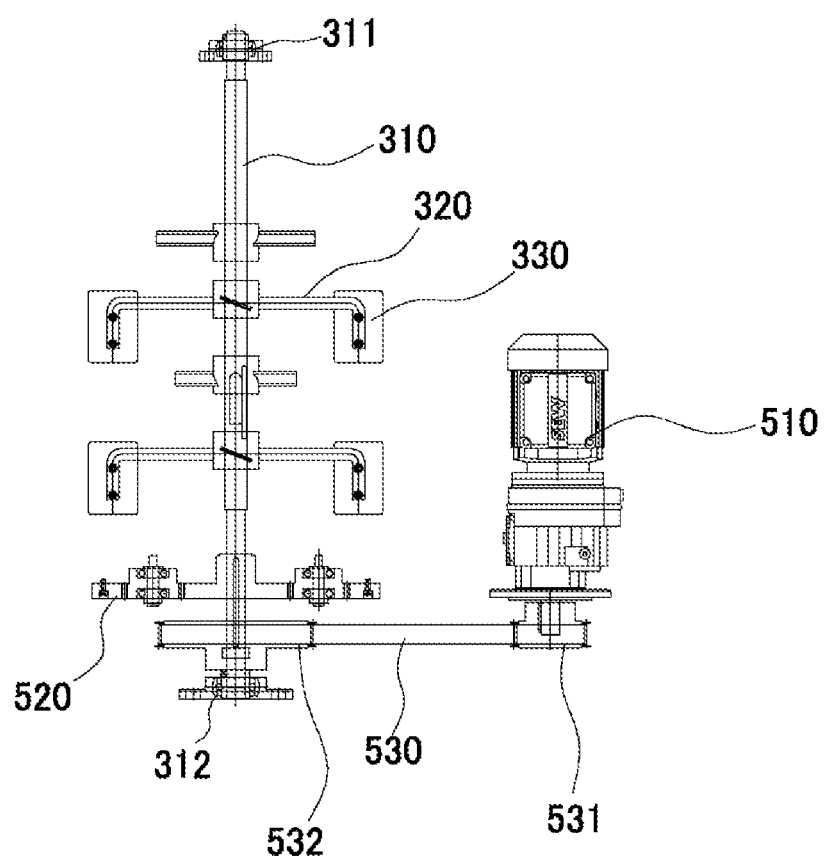
FIG. 6 is a diagram provided to explain a stirring unit and a rotation driving unit in accordance with an exemplary embodiment of the present disclosure.
Figure 7:
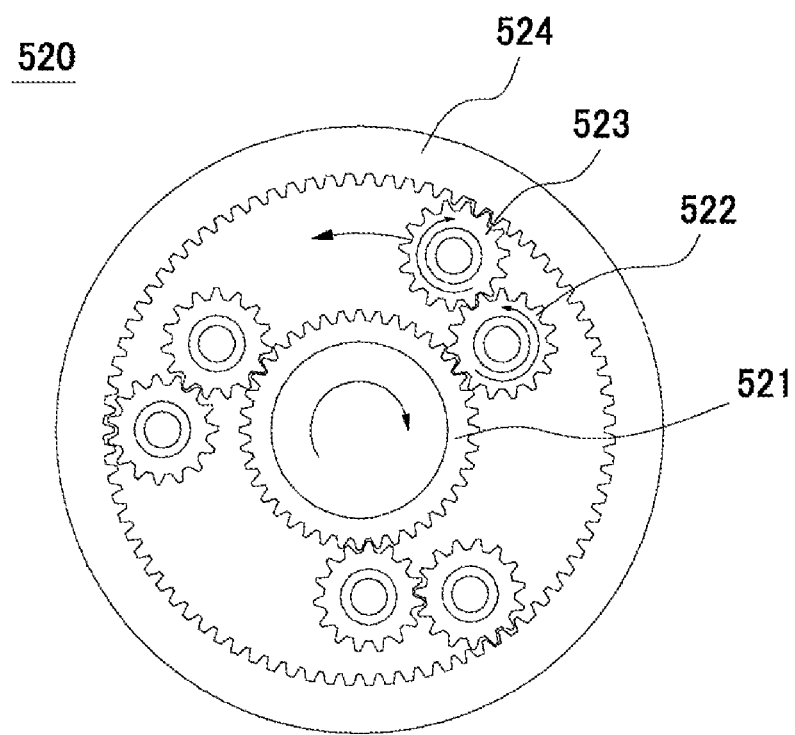
FIG. 7 is a diagram provided to explain a planet gear unit in accordance with an exemplary embodiment of the present disclosure.
Figure 8:
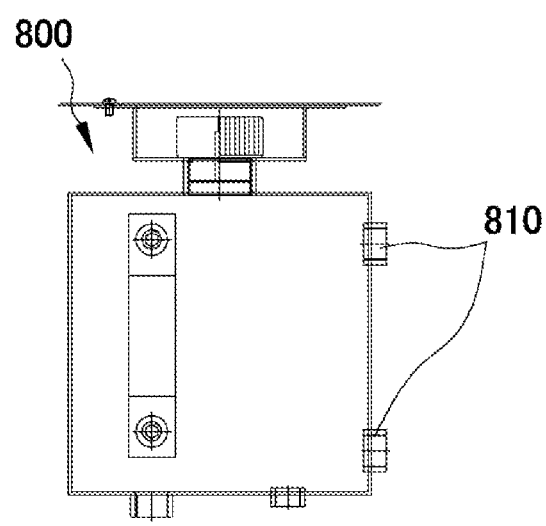
FIG. 8 is a front view of a drug tank in accordance with an exemplary embodiment of the present disclosure.
Figure 9:
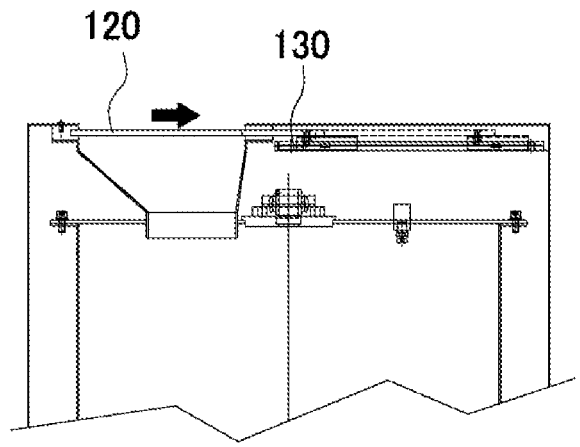
FIG. 9 is a side view of an opening/closing door in accordance with another exemplary embodiment of the present disclosure.
Figure 10:
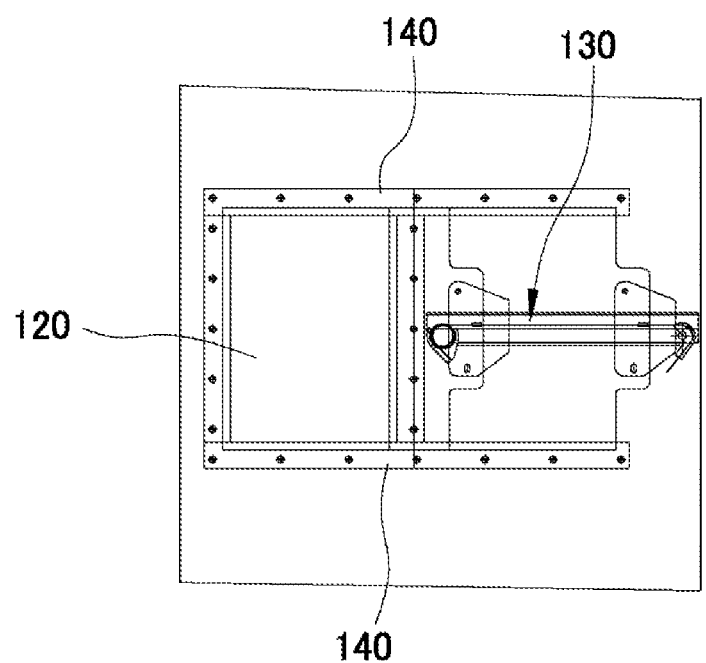
FIG. 10 is a plane view of an opening/closing door in accordance with another exemplary embodiment of the present disclosure.
Figure 11:
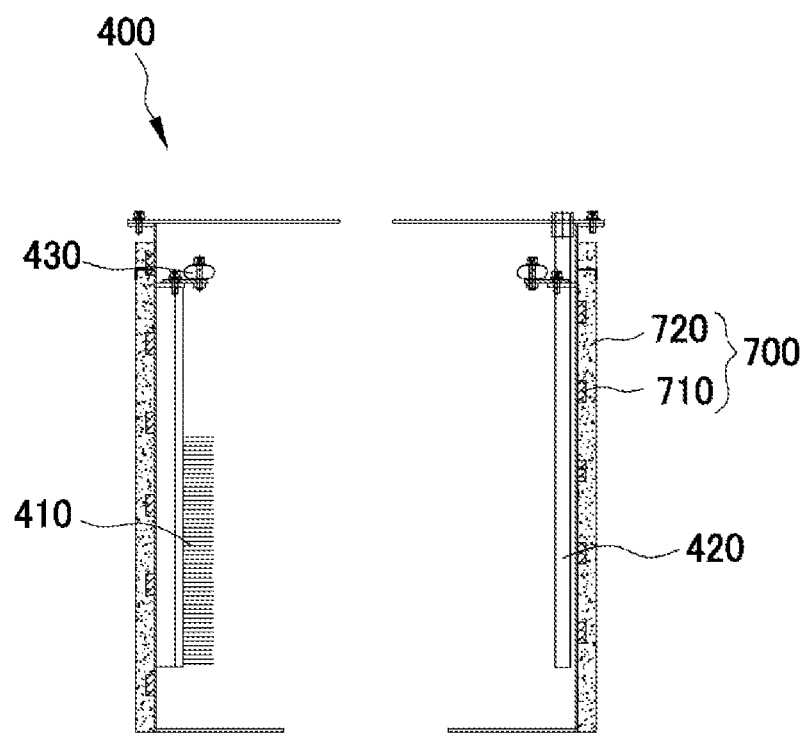
FIG. 11 is a cross-sectional view of an outer chamber in accordance with an exemplary embodiment of the present disclosure.

FIG. 1 is a front view of a food waste treatment apparatus in accordance with an exemplary embodiment of the present disclosure, FIG. 2 is a side view of a food waste treatment apparatus in accordance with an exemplary embodiment of the present disclosure, FIG. 3 is a perspective view of an inner chamber in accordance with an exemplary embodiment of the present disclosure, FIG. 4 is a cross-sectional view of an inner chamber in accordance with an exemplary embodiment of the present disclosure, FIG. 5 is a plane view of a food waste treatment apparatus in accordance with an exemplary embodiment of the present disclosure, FIG. 6 is a diagram provided to explain a stirring unit and a rotation driving unit in accordance with an exemplary embodiment of the present disclosure, FIG. 7 is a diagram provided to explain a planet gear unit in accordance with an exemplary embodiment of the present disclosure, FIG. 8 is a front view of a drug tank in accordance with an exemplary embodiment of the present disclosure, FIG. 9 is a side view of an opening/closing door in accordance with another exemplary embodiment of the present disclosure, FIG. 10 is a plane view of an opening/closing door in accordance with another exemplary embodiment of the present disclosure, and FIG. 11 is a cross-sectional view of an outer chamber in accordance with an exemplary embodiment of the present disclosure.

Firstly, a food waste treatment apparatus 10 (hereinafter, referred to as "the present food waste treatment apparatus 10") in accordance with an exemplary embodiment of the present disclosure will be described.

Referring to FIG. 1 and FIG. 2, the present food waste treatment apparatus 10 includes a housing 100, an inner chamber 200, a stirring unit 300, an outer chamber 400, and a rotation driving unit 500.

The housing 100 includes a food inlet opening 110 at its top surface.

Further, the food inlet opening 110 includes a hopper-shaped inlet guide unit 111 as illustrated in FIG. 2, and, thus, food can be readily put into the inner chamber 200.

Referring to FIG. 1, the present food waste treatment apparatus 10 may include the inner chamber 200 where food waste introduced through the food inlet opening 110 is collected.

The inner chamber 200 may be manufactured into a shape having a predetermined shape with an open top. For example, as illustrate in FIG. 1, the inner chamber 200 may be formed into a cylindrical shape.

At a lower portion of the inner chamber 200, multiple drainage holes 210 through which leachate generated during degradation of food waste is discharged may be formed.

Further, the inner chamber 200 and the stirring unit 300 may be rotated in opposite directions. Therefore, the food waste introduced into the inner chamber 200 can be stirred readily. Details thereof will be described later.

The present food waste treatment apparatus 10 may include the stirring unit 300 provided within the inner chamber 200 and configured to stir food waste. Details of the stirring unit 300 will be described later.

The present food waste treatment apparatus 10 may include the outer chamber 400 positioned outside the inner chamber 200. For example, the outer chamber 400 may be manufactured into a cylindrical shape in the same manner as the inner chamber 200.

The leachate discharged through the drainage holes 210 of the inner chamber 200 may fall into the outer chamber 400 and may be collected therein. Further, referring to FIG. 2, the leachate collected in the outer chamber 400 may be discharged to the outside through a drainpipe 620. For example, the leachate may be discharged to a BOD purifier or the like through a drainpipe 620.

After completion of stirring and drying the food waste, food waste residue may be discharged to the outside of the housing 100 through a separate discharge hole or a discharge device and then used as compost for growing plants.

The rotation driving unit 500 may rotate the stirring unit 300 and the inner chamber 200 in opposite directions. Therefore, the present food waste treatment apparatus 10 may have the improved efficiency in stirring food waste introduced into the inner chamber 200.

Hereinafter, referring to FIG. 3 and FIG. 4, the inner chamber 200 in accordance with an exemplary embodiment of the present disclosure will be described.

As described above, the food waste introduced through the food inlet opening 110 is collected in the inner chamber 200.

Further, the inner chamber 200 may include the multiple drainage holes 210 at its lower circumferential portion and bottom portion.

To be specific, the food waste introduced into the inner chamber 200 may be degraded by microorganisms or degrading materials. Further, leachate generated during the degradation may be discharged to the outer chamber 400 through the drainage holes 210 formed in the inner chamber 200.

Furthermore, the inner chamber 200 may include a scrapper 220 at its lower portion in order for leachate and sludge collected in the outer chamber 400 to be discharged through the drainpipe 620.

To be specific, the scrapper 220 may be fixed at a lower surface of the inner chamber 200, and multiple scrappers 220 may be provided to have a predetermined angle around a rotation shaft 310.

Further, when the inner chamber 200 is rotated, the scrapper 220 may be brought into close contact with a bottom surface of the outer chamber 400 and thus may discharge the leachate and sludge positioned at a lower portion of the outer chamber 400 through the drainpipe 620.

Hereinafter, referring to FIG. 2 and FIG. 5, the outer chamber 400 in accordance with an exemplary embodiment of the present disclosure will be described.

As described above, the outer chamber 400 includes the inner chamber 200 therein, and may collect the leachate discharged through the drainage holes 210 of the inner chamber 200. For example, the outer chamber 400 may have a cylindrical shape in the same manner as the inner chamber 200.

Further, the outer chamber 400 may include a brush unit 410 and a vertical cleaning pipe 420 positioned between the outer chamber 400 and the inner chamber 200.

The brush unit 410 may be positioned between the outer chamber 400 and the inner chamber 200 and extended vertically.

The brush unit 410 is in contact with an outer surface of the inner chamber 200, and cleans the outer surface of the inner chamber 200 when the inner chamber 200 is rotated.

For example, as illustrated in FIG. 5, the brush unit 410 may include a brush fixing unit extended vertically on an inner surface of the outer chamber 400 and a brush inserted and fixed to the brush fixing unit. Herein, the brush may be positioned corresponding to the drainage holes 210 formed in a circumferential surface of the inner chamber 200. Further, the brush units 410 may be placed 180 degrees apart from each other around the rotation shaft 310, but may not be limited thereto.

The vertical cleaning pipe 420 may be positioned adjacent to the brush unit 410 and configured to inject warm water to an outer circumferential surface of the inner chamber 200.

The vertical cleaning pipe 420 may inject warm water to the brush unit 410 and thus increase the capability of cleaning the outer surface of the inner chamber 200.

For example, the present food waste treatment apparatus 10 includes a water supply unit 101 that is supplied with water from the outside and a water heating unit (not illustrated) that heats the supplied water, and, thus, may supply warm water heated by the water heating unit to the vertical cleaning pipe 420.

Further, the outer chamber 400 may include at least one guide roller 430 fixed on the inner surface of the outer chamber 400 and configured to guide a rotation movement of the inner chamber 200.

The guide rollers 430 may be placed a predetermined angle apart from each other around the rotation shaft 310 and configured to guide a rotation movement of the inner chamber 200 while being in contact with the outer surface of the inner chamber 200. For example, the guide rollers 430 may be placed 120 degrees apparat from each other as illustrated in FIG. 5, but may not be limited thereto.

Hereinafter, referring to FIG. 6 and FIG. 7, the stirring unit 300 and the rotation driving unit 500 in accordance with an exemplary embodiment of the present disclosure will be described.

The stirring unit 300 may include the rotation shaft 310, multiple stirring blade supporting bars 320, and stirring blades 330.

The rotation shaft 310 may be rotated as being connected to the rotation driving unit 500.

Further, the rotation shaft 310 may include at least bearing 311 provided along the circumference of an outer peripheral surface of one end and at least one bearing 312 provided along the circumference of an outer peripheral surface of the other end. Therefore, damage to the rotation shaft 310 can be suppressed.

The multiple stirring blade supporting bars 320 may be vertically separated from each other and extended from the rotation shaft 310 in a direction perpendicular to the rotation shaft 310.

The stirring blades 330 may be provided at ends of the respective stirring blade supporting bars 320.

For example, the stirring blade 330 may be provided at the stirring blade supporting bar 320 via a connection member. Further, the connection member may be implemented as a bolt or a casting mold.

In the present food waste treatment apparatus 10, food waste is stirred by rotation of the stirring blade supporting bars 320 and the stirring blades 330, and, thus, the food waste can be suppressed from leaning to one side within the housing 100.

Further, the food waste stirred and dried by the stirring blade supporting bars 320 and the stirring blades 330 may be degraded by microorganisms or degrading materials introduced into the inner chamber 200. Herein, leachate generated during the degradation may be discharged to the outer chamber 400 through the drainage holes 210.

The rotation driving unit 500 includes a motor 510, a planet gear unit 520, and a belt unit 530.

The motor 510 may supply power for rotating the stirring unit 300 and the inner chamber 200.

The belt unit 530 may transfer the power from the motor 510 to the planet gear unit 520.

To be specific, the belt unit 530 may be placed to pass through a starting sprocket 531 provided at a rotation shaft of the motor 510 and an interlocking sprocket 532 provided along an outer periphery of one end of the rotation shaft 310. Therefore, if the motor 510 is operated and the starting sprocket 531 is rotated, the interlocking sprocket 532 may be rotated. If the interlocking sprocket 532 is rotated, the rotation shaft 310 is rotated, and, thus, the stirring blade supporting bars 320 and the stirring blades 330 may be rotated.

The planet gear unit 520 may receive the power through the belt unit 530 and rotate the stirring unit 300 and the inner chamber 200.

Further, the planet gear unit 520 may rotate the stirring unit 300 and the inner chamber 200 in opposite directions.

Referring to FIG. 7, in order to do so, the planet gear unit 520 may include a sun gear 521 connected to the rotation shaft 310 of the stirring unit 300 and configured to transfer a rotation power, multiple first planet gears 522 engaged with the sun gear 521, multiple second planet gears 523 respectively engaged with the first planet gears 522, and a ring gear 524 engaged with the second planet gears 523 and including a gear at an inner periphery.

Further, the inner chamber 200 may be connected to the first planet gears 522 or the second planet gears 523, and the rotation shaft 310 of the stirring unit 300 may be connected to the sun gear 521.

For example, the sun gear 521 may receive power from the motor 510 and may be rotated clockwise. In this case, the rotation shaft 310 connected to the sun gear 521 may be rotate clockwise. Further, the first planet gears 522 may be rotated counterclockwise as being engaged with the sun gear 521, and the second planet gears 523 may be rotate clockwise as being respectively engaged with the first planet gears 522. Herein, the first and second planet gears 522 and 523 may be moved counterclockwise, and, thus, the inner chamber 200 connected to the first planet gears 522 or second planet gears 523 may be rotate counterclockwise.

Accordingly, the inner chamber 200 and the rotation shaft 310 may be rotated in opposite directions.

Referring to FIG. 1 and FIG. 8, the present food waste treatment apparatus 10 may further include a drug tank 800 configured to store microorganism or degrading materials to be supplied into the inner chamber 200 to degrade food waste. Further, the drug tank 800 may include a level sensor 810 configured to measure a level of the microorganism or degrading materials.

For example, the level sensor 810 may sense that a level of the microorganism or degrading materials in the drug tank 800 is equal to or less than a predetermined level. In this case, an alarm message may be displayed on a control unit 900 provided at an outer surface of the housing 100.

An opening/closing door 120 in accordance with another exemplary embodiment of the present disclosure will be described with reference to FIG. 1 and FIG. 9.

The food waste treatment apparatus 10 may include the opening/closing door 120 and a door driving unit 130 configured to drive the opening/closing door 120.

To be specific, the opening/closing door 120 may be automatically opened or closed by the door driving unit 130.

The opening/closing door 120 may have a hinge-type structure as illustrated in FIG. 1.

Further, the opening/closing door 120 may be a sliding door as illustrated in FIG. 9 and FIG. 10.

To be specific, the opening/closing door 120 may slide and move to open/close the food inlet opening 110. Herein, a door guide unit 140 may be provided on both sides of the opening/closing door 120 to guide a sliding movement. For example, the opening/closing door 120 may be formed of steel use stainless (SUS) and the door guide unit 140 may be formed of acetal resin.

Referring to FIG. 1, the present food waste treatment apparatus 10 may further include at least one shower nozzle unit 610.

The shower nozzle unit 610 may be configured to supply warm water into the inner chamber 200 to help with the microbic activity and a destruction process within the inner chamber 200.

The present food waste treatment apparatus 10 may further include a temperature controller 700 configured to control a temperature within the outer chamber 400.

Referring to FIG. 11, the temperature controller 700 may include a trace heater 710 wound around an outer surface of the outer chamber 400 and a lagging material 720 surrounding the trace heater 710 and the outer surface of the outer chamber 400.

For example, the temperature controller 700 may set a temperature through the control unit 900 provided outside.

Referring to FIG. 5, the present food waste treatment apparatus 10 may further include the control unit 900 which is provided at the outer surface of the housing 100 and configured to display multiple control menus and status information of the food waste treatment apparatus 10 and through which the displayed control menus can be selected. For example, the control unit 900 may be a touch screen.

The control unit 900 may display a menu for automatic operation of the present food waste treatment apparatus 10, a menu for displaying the overall operation status, a menu for test run of each function, a menu for setting operation parameters, a menu for displaying an alarm message, and a menu for setting each function.

For example, a user may select the menu for setting each function and set a temperature of the inner chamber 200. In other words, if a temperature of the inner chamber 200 is equal to or less than a preset temperature, the temperature of the inner chamber 200 may be increased using the temperature controller 700. Further, if the temperature of the inner chamber 200 is equal to or more than the preset temperature, the microorganisms within the inner chamber 200 may not act, and, thus, the operation may be stopped for a while.

Status information of the present food waste treatment apparatus 10 may be collected by an external server through a network.

To be specific, the collected status information of the present food waste treatment apparatus 10 may include the overall status information of the present food waste treatment apparatus 10 such as an input amount of food waste, a throughput of food waste, an amount of water used, and an amount of electricity used.

Further, the status of the present food waste treatment apparatus 10 may be remotely monitored and remotely controlled through the network.

Particularly, in the USA, a user may lease and use the present food waste treatment apparatus 10. In this case, the amount of food waste treated by the present food waste treatment apparatus 10 may be transmitted to or stored in the external server. A bill may be issued to the user on the basis of the transmitted or stored information.

Further, as described above, the amount of food waste treated by the present food waste treatment apparatus 10 may be measured daily, weekly, and monthly. Thus, a bill may be issued to the user on any one of daily, weekly, and monthly basis.

Furthermore, the control unit 900 may display the status information of the food waste treatment apparatus 10 to be transmitted to or stored in the external server.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

EXPLANATION OF CODES

10: Food waste treatment apparatus
100: Housing
110: Food inlet opening
120: Opening/closing door
130: Door driving unit
140: Door guide unit
200: Inner chamber
210: Drainage hole
220: Scrapper
230: Bearing
300: Stirring unit
310: Rotation shaft
311, 312: Bearing
320: Stirring blade supporting bar
330: Stirring blade
400: Outer chamber
410: Brush unit
420: Vertical cleaning pipe
430: Guide roller
500: Rotation driving unit
510: Motor
520: Planet gear unit
521: Sun gear
522: First planet gear
523: Second planet gear
524: Ring gear
530: Belt unit
610: Shower nozzle unit
620: Drainpipe
700: Temperature controller
710: Trace heater
720: Lagging material
800: Drug tank
810: Level sensor
900: Control unit

I claim:

1. A food waste treatment apparatus comprising:
a housing including a food inlet opening at its top surface;
an inner chamber where food waste introduced through the food inlet opening is collected;
a stirring unit provided within the inner chamber and configured to stir the food waste;
an outer chamber positioned outside the inner chamber; and
a rotation driving unit configured to rotate the stirring unit and the inner chamber,
at least one brush unit positioned between the outer chamber and the inner chamber and extended vertically; and
a vertical cleaning pipe positioned adjacent to the brush unit and configured to inject warm water to an outer circumferential surface of the inner chamber;
wherein the inner chamber includes:
multiple drainage holes at its lower circumferential portion and bottom portion;
multiple scrappers positioned at a lower portion of the inner chamber in order for leachate and sludge collected in the outer chamber to be discharged through a drainpipe, and
wherein the inner chamber and the stirring unit are rotated by the rotation driving unit in opposite directions.

2. The food waste treatment apparatus of claim 1,
wherein the stirring unit includes:
a rotation shaft;
multiple stirring blade supporting bars separated from each other and extended from the rotation shaft in a direction perpendicular to the rotation shaft; and
a stirring blade provided at an end of each of the stirring blade supporting bars.

3. The food waste treatment apparatus of claim 2,
wherein the rotation shaft includes at least one bearing provided along the circumference of an outer peripheral surface of one end and at least one bearing provided along the circumference of an outer peripheral surface of the other end.

4. The food waste treatment apparatus of claim 1,
wherein the rotation driving unit includes:
a motor configured to supply power;
a planet gear unit connected to the stirring unit and the inner chamber; and
a belt unit configured to transfer the power from the motor to the planet gear unit.

5. The food waste treatment apparatus of claim 4,
wherein the planet gear unit includes:
a sun gear connected to a rotation shaft of the stirring unit and configured to transfer rotation power;
multiple first planet gears engaged with the sun gear;
multiple second planet gears respectively engaged with the first planet gears; and
a ring gear engaged with the second planet gears and including a gear at an inner periphery.

6. The food waste treatment apparatus of claim 5,
wherein the inner chamber is connected to the first planet gears or second planet gears, and the stirring unit is connected to the sun gear.

7. The food waste treatment apparatus of claim 1, further comprising:
at least one shower nozzle positioned above the inner chamber and configured to inject and supply warm water into the inner chamber.

8. The food waste treatment apparatus of claim 1,
wherein the outer chamber includes:
at least one guide roller fixed on an inner surface of the outer chamber and configured to guide a rotation movement of the inner chamber.

9. The food waste treatment apparatus of claim 1, further comprising:
a temperature controller at an outer peripheral surface of the outer chamber,
wherein the temperature controller includes:
a trace heater wound around an outer surface of the outer chamber; and
a lagging material surrounding the trace heater and the outer surface of the outer chamber.

10. The food waste treatment apparatus of claim 1, further comprising:
an opening/closing door configured to open/close the food inlet opening; and
a door driving unit configured to drive the opening/closing door,
wherein the opening/closing door slides and moves to open/close the food inlet opening.

11. The food waste treatment apparatus of claim 1, further comprising:
a drug tank configured to store microorganism or degrading materials to be supplied into the inner chamber to degrade food waste.

12. The food waste treatment apparatus of claim 11,
wherein the drug tank includes:
a level sensor configured to measure a level of the microorganism or degrading materials.

13. The food waste treatment apparatus of claim 1, further comprising:
a control unit which is provided at an outer surface of the housing and configured to display multiple control menus and status information of the food waste treatment apparatus and through which the displayed control menus are selected.

14. The food waste treatment apparatus of claim 13,
wherein the control unit is configured to display the status information of the food waste treatment apparatus to be transmitted to or stored in an external server.

15. The food waste treatment apparatus of claim 1,
wherein the food inlet opening includes:
a hopper-shaped inlet guide unit.

* * * * *